United States Patent

Cooper

(10) Patent No.: US 7,410,467 B2
(45) Date of Patent: Aug. 12, 2008

(54) ACTIVE IMPLANTABLE MEDICAL DEVICE INCLUDING MEANS FOR THE EVALUATION OF INTRACARDIAC VOLUME

(75) Inventor: Daniel Cooper, Saint Ismier (FR)

(73) Assignee: ELA Medical S.A.S., Montrouge (FR)

( * ) Notice: Subject to any disclaimer, the term of this patent is extended or adjusted under 35 U.S.C. 154(b) by 208 days.

(21) Appl. No.: 11/206,624

(22) Filed: Aug. 18, 2005

(65) Prior Publication Data

US 2006/0116591 A1    Jun. 1, 2006

(30) Foreign Application Priority Data

Aug. 18, 2004   (FR)   ................................. 04 08955

(51) Int. Cl.
    *A61B 5/02*    (2006.01)
(52) U.S. Cl. .................................................. 600/508
(58) Field of Classification Search ................ 600/508, 600/547, 554
    See application file for complete search history.

(56) References Cited

U.S. PATENT DOCUMENTS

| | | | | |
|---|---|---|---|---|
| 4,702,253 A | * | 10/1987 | Nappholz et al. | 607/20 |
| 4,919,136 A | * | 4/1990 | Alt | 607/20 |
| 5,427,113 A | * | 6/1995 | Hiroshi et al. | 600/547 |
| 6,186,955 B1 | * | 2/2001 | Baura | 600/526 |
| 6,438,408 B1 | * | 8/2002 | Mulligan et al. | 600/510 |
| 6,604,002 B2 | | 8/2003 | Molin | |
| 6,725,091 B2 | * | 4/2004 | Dal Molin | 607/2 |
| 2001/0034540 A1 | * | 10/2001 | Molin | 607/20 |
| 2002/0115939 A1 | * | 8/2002 | Mulligan et al. | 600/510 |
| 2004/0127944 A1 | | 7/2004 | Casset | |
| 2004/0147968 A1 | | 7/2004 | Casset | |

FOREIGN PATENT DOCUMENTS

| | | | |
|---|---|---|---|
| EP | 1 116 497 A1 | 7/2001 | |
| EP | 1 138 346 A1 | 10/2001 | |

* cited by examiner

*Primary Examiner*—Carl Layno
*Assistant Examiner*—Jon-Eric C. Morales
(74) *Attorney, Agent, or Firm*—Orrick Herrington & Sutcliffe, LLP

(57) ABSTRACT

An active implantable medical device having a plurality of connection terminals able to be connected to electrodes placed in at least three distinct respective sites in a myocardium; circuits for measuring an intracardiac bio-impedance, comprising circuits for injecting a current and circuits for collecting a voltage at respective poles of a configuration of said connection terminals, and circuits able to deliver at an output a dynamic impedance signal that is a function of the injected current and the collected voltage; and circuits for evaluating an intracardiac volume, receiving at in input the impedance signal and delivering at an output a dynamic value of volume representing an instantaneous absolute value of intracardiac volume.

4 Claims, 1 Drawing Sheet

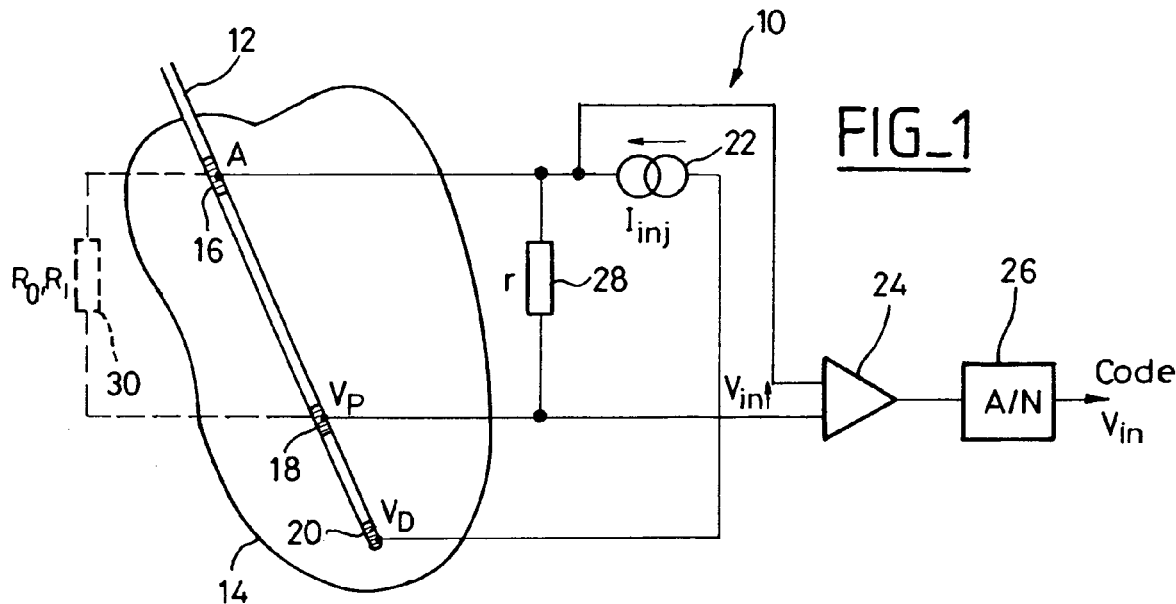
FIG_1
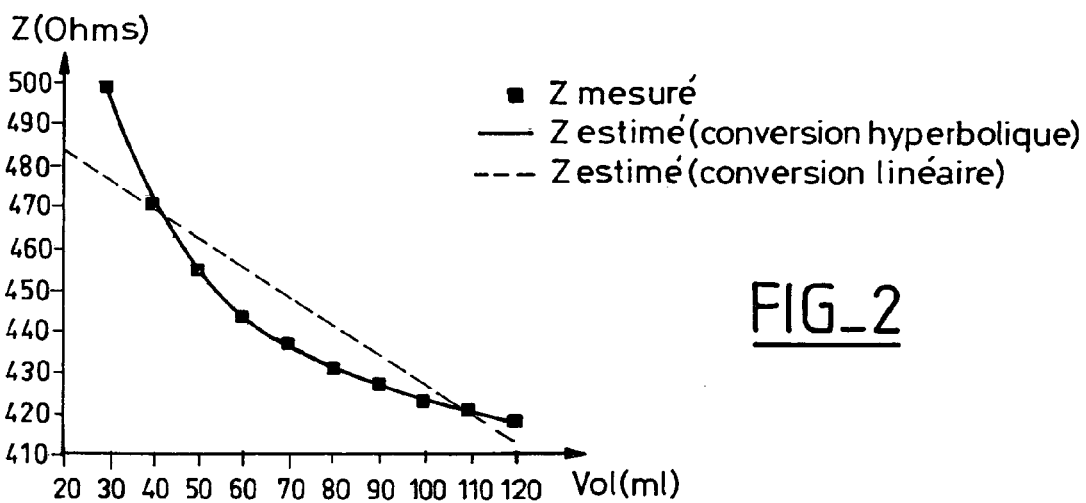
FIG_2
- ■ Z mesuré
- —— Z estimé (conversion hyperbolique)
- --- Z estimé (conversion linéaire)
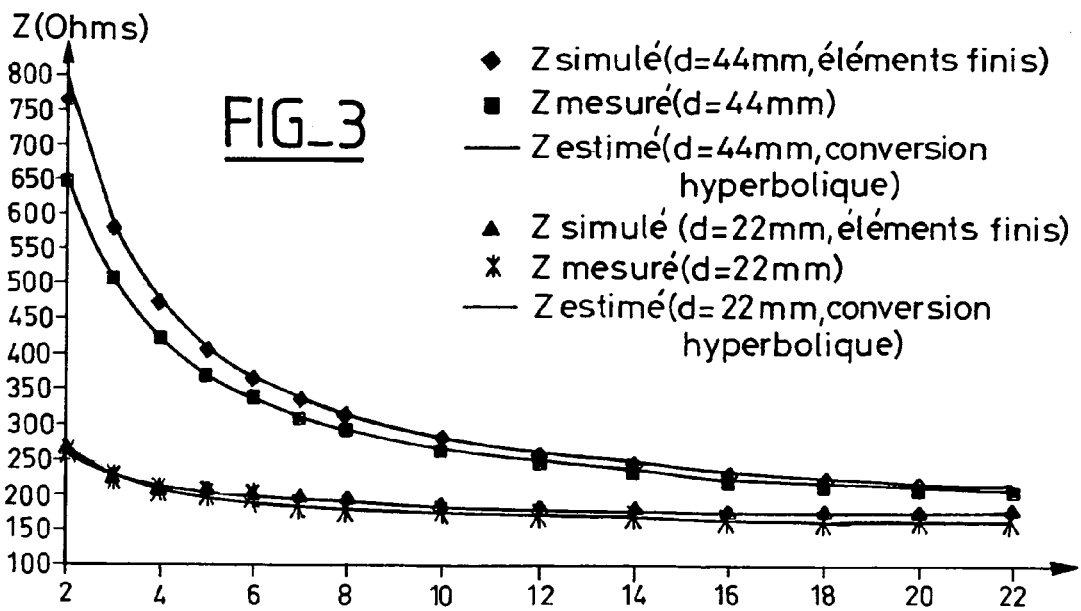
FIG_3
- ♦ Z simulé (d=44mm, éléments finis)
- ■ Z mesuré (d=44mm)
- —— Z estimé (d=44mm, conversion hyperbolique)
- ▲ Z simulé (d=22mm, éléments finis)
- ✳ Z mesuré (d=22mm)
- —— Z estimé (d=22mm, conversion hyperbolique)

ACTIVE IMPLANTABLE MEDICAL DEVICE INCLUDING MEANS FOR THE EVALUATION OF INTRACARDIAC VOLUME

FIELD OF THE INVENTION

The present invention relates to "active implantable medical devices" as defined by the Jun. 20, 1990 directive 90/385/CEE of the Council of European Communities, and more precisely to devices known as cardiac pacemakers, defibrillators, and/or cardiovertors that are able to deliver to the heart pulses of low energy for treatment of cardiac rhythm disorders. The invention relates in particular to devices of this type that measure an intracardiac bio-impedance, typically the measurement of a trans-valvular, trans-septum or intra-ventricular bio-impedance, using known techniques.

BACKGROUND OF THE INVENTION

Intracardiac bio-impedance is a parameter correlated with cardiac flow, and thus with the ejection fraction, which are parameters that can be useful in controlling certain stimulation parameters such as heart rate and/or atrio-ventricular delay in a direction making it possible to maximize flow, or in controlling inter-ventricular delay in the case of a biventricular stimulation.

EP-A-1116497 and its counterpart U.S. Pat. No. 6,604,002 (which U.S. patent is incorporated herein by reference), both assigned herewith to ELA Médical, Montrouge, France, describe a dynamic measurement of intracardiac trans-valvular bio-impedance (i.e., between an atrium and a ventricle located on the same side of the heart). EP-A-1138346 and its counterpart U.S. Pat. No. 6,725,091 (which U.S. patent is incorporated herein by reference), both assigned herewith to ELA Médical, Montrouge, France, describe measurement of a trans-septum bio-impedance (i.e., between a site located on one side of the heart and a site located on other side of the heart), such configuration capable of being an oblique trans-septum configuration (i.e., between a ventricle on one side of the heart and an atrium located on the opposite side) or an interventricular trans-septum configuration (i.e., between the two ventricles).

The intracardiac bio-impedance is measured by injection of a current and collection of a voltage at respective poles in a tripolar or quadripolar configuration of electrodes placed inside the myocardium (atrial electrode, ventricular proximal electrode, ventricular distal electrode, etc). The bio-impedance, no matter how it is measured, is a dynamic parameter (i.e., it varies continuously during the same cardiac cycle) giving an indication of the instantaneous cardiac flow. More precisely, variations of intracardiac bio-impedance depend mainly on variations of the volume of the cardiac cavities, a low impedance corresponding to a high volume, and a high impedance corresponding to a low volume. The impedance thus varies between a minimum, reached at the end of the diastolic phase, and a maximum, reached at the end of the systolic phase. The difference between the systolic impedance and the diastolic impedance gives a value correlated to the ejection volume, a value from which one can evaluate the cardiac flow, which is the product of the ejection volume multiplied by the heart rate. The indications provided by these measurements are relative indications of the systolic and diastolic volumes, i.e., one determines the difference between these volumes, which, with the knowledge of the rate, is sufficient if one only wishes to evaluate the cardiac flow. On the other hand, these devices do not give access to an absolute measurement of intracardiac volume.

The starting point of the present invention is the observation that, in certain circumstances, it may be useful for diagnostic purposes to have a signal representing an absolute measurement of intracardiac volume. Until now, the absolute value of intracardiac volume has been estimated starting from echographic signals, which make it possible to evaluate the diastolic volume and the systolic volume, i.e., the two extreme values of intracardiac volume, and gives an indication of the way in which volume varies between these two extremes during the same cycle. However, this technique is applicable only when the patient undergoes an examination, which does not allow a permanent follow-up, over the long term. Further, the values obtained are computed values, which are posted or printed by the echographic device but do not constitute signals that could, for example, allow controlling of a function of a pacemaker or a diagnosis of certain pathologies by analysis of evolution of this signal.

OBJECTS AND SUMMARY OF THE INVENTION

The present invention proposes an active implantable medical device capable of evaluating the absolute instantaneous value of the intracardiac volume, which addresses the above-identified disadvantages.

To this end, the invention proposes a device of the type described in particular in the above-mentioned EP-A-1116497 and EP-A-1138346 and their respective counterparts, U.S. Pat. Nos. 6,604,002 and 6,725,091, i.e., including: a plurality of connection terminals able to be connected to electrodes placed in at least three distinct respective sites of a myocardium, and means for measuring an intracardiac bio-impedance, including means for injecting a current and collecting a voltage at respective poles of a configuration of the aforesaid terminals, and means able to deliver at an output a dynamic impedance signal that is a function the injected current and the corresponding collected voltage.

The device can also include means for evaluating the intracardiac volume, receiving at an input the impedance signal, and delivering at the output a dynamic value of the volume, representative of the instantaneous absolute value of an intracardiac volume.

In a first embodiment of the invention, the means for evaluating are means able to operate the conversion of the impedance signal into a volume according to a linear characteristic in the form:

$$\text{Vol} = (a*Z) + b$$

(Vol being the value of volume delivered by the means for evaluating, Z being the value of the impedance signal received at the input, and a and b being constants).

In a second, preferred, embodiment of the invention, the means for evaluating are means able to operate the conversion of the impedance signal into volume according to a hyperbolic characteristic in the form:

$$\text{Vol} = a/(Z+b)$$

(Vol being the value of volume delivered by the means for evaluating, Z being the value of the impedance signal received in input, and a and b being constants).

In either the first or second embodiment, calibration means can determine beforehand the aforementioned constants a and b starting from at least two sets of recorded values of volume and measured corresponding impedance values.

BRIEF DESCRIPTION OF THE DRAWINGS

Further benefits, features, and characteristics of the present invention will become apparent to a person of ordinary skill in the art in view of the following detailed description of the invention, made with reference to the annexed drawings wherein:

FIG. 1 schematically illustrates an example of a technique for measuring an intracardiac bio-impedance;

FIG. 2 is an impedance/volume diagram showing results obtained using the technique of the present invention, respectively for a linear conversion and a hyperbolic conversion, compared to values actually measured in the case of a real clinical trial; and FIG. 3 is a diagram showing, by way of comparison with the results shown in FIG. 2, the results of a digital simulation by the method of finite elements.

DETAILED DESCRIPTION OF THE INVENTION

With regard to its software aspects, the present invention can be implemented by suitable programming of the control software of known pacemakers. The invention can in particular be applied to the implantable devices marketed by ELA Médical, Montrouge, France, such as the Symphony and Rhapsody branded devices. These are programmable devices with memory and microprocessors comprising circuits for receiving, formatting, and processing electric signals collected by implanted probes bearing cardiac electrodes, and delivering stimulation impulses to these electrodes. It is possible to transmit to the device by telemetry the software, which will be stored and carried out to implement the functions of the invention described below. Adaptation of these apparatuses and creation of suitable software programming to implement the functions of the inventions described herein are deemed to be within the abilities of a person of ordinary skill in the art and a matter of design choice and will not be described in detail herein.

In FIG. 1, reference number 10 indicates, generally, an intracardiac bio-impedance measuring circuit, incorporated in the circuit of the implanted generator. Reference number 12 indicates an endocavitary probe implanted in the myocardium 14 and comprising, in the illustrated example, an atrial electrode 16, a proximal ventricular electrode 18, and a distal ventricular electrode 20.

For measurement of the intracardiac impedance (in this example a trans-valvular impedance), the device injects by means of generator 22 a current $I_{inj}$ between the atrial electrode 16 and the distal ventricular electrode 20. A corresponding voltage $V_{in}$ is then collected between the atrial electrode 16 (which is thus an electrode common to both the injection and the collection) and the proximal ventricular electrode 18. This voltage is amplified by an amplifier 24 and digitized by an analog/digital converter 26, to give a coded value representative of the voltage $V_{in}$. This measurement technique in itself is known and therefore will not be described more in anymore detail. One will note that the described technique is only one example of an intracardiac configuration of bio-impedance measurement.

The first stage (in itself known) of treatment of the signals consists of evaluating the impedance starting from the values of the injected current $I_{inj}$ and of the collected differential voltage $V_{in}$. This impedance is given by the relation:

$$Z = \frac{K_1 * (V_{in} - K_3)}{I_{inj}} - K_2$$

($K_1$ being the factor of proportionality between the input voltage and a step of converter 26 (expressed in µV), $K_2$ being the internal impedance of the implant, symbolically illustrated as 28 by resistance R (expressed in ohms), and $K_3$ being the shift value, i.e., the value delivered by converter 26 for a null voltage $V_{in}$ in input (expressed in step of code).

To determine the three constants $K_1$, $K_2$, and $K_3$, it is necessary to operate beforehand three measurements with different values $I_{inj1}$ and $I_{inj2}$ from the injection current and values different from the impedance between the terminals. This calibration can be carried out, for example, by substituting at probe 12 a resistance 30 of a fixed known value $R_0$ or $R_1$, one of the two values being able to be for example $R_0=0$ (short-circuiting the input).

Calibration can be carried out for each implant, during a test automated on a production line, the specific values of the constants $K_1$, $K_2$, and $K_3$ being memorized in the implant after being determined:

$K_1$ is the drift of the input voltage for step I of the converter, expressed in µV by step of code:

$$K_1 = \frac{I_{inj2} * R_1}{(V_{in}(R_1, I_{inj2}) - V_{in}(R_0, I_{inj2}))}$$

$K_2$ is the internal impedance of the implant, expressed in ohms:

$$K_2 = \frac{(V_{in}(R_0, I_{inj2}) - V_{in}(R_0, I_{inj1})) * K_1}{(I_{inj2} - I_{inj1})}$$

$K_3$ is the value of exit of the converter for a voltage of null input (expressed in step of code):

$$K_3 = \frac{V_{in}(R_1, I_{inj2}) - (R_1 + K_2) * I_{inj2}}{K_1}$$

In the alternative, it is possible to carry out a calibration only for some representative samples of implants, to determine an average value for the constants $K_1$, $K_2$, and $K_3$, and to then apply these constants to all implants. This last manner of proceeding is less precise, but appears in practice sufficient for most current needs, except for some research protocols requiring a higher precision.

The following stage, characteristic of the present invention, concerns determining the absolute dynamic value of the endocavitary volume starting from the impedance signal thus obtained.

In the first embodiment, volume (Vol) is given starting from a linear volume/impedance characteristic, i.e., a relation of the general form Vol=(a*Z)+b. To determine the two constants a and b, a calibration is carried out starting from two initial known points, determined for each patient, for example, the systolic volume $Vol_1$ and diastolic volume $Vol_2$, determined by echography. These two volume values $Vol_1$ and $Vol_2$, correspond to impedance values $Z_1$ and $Z_2$, as follows:

$$Vol = Vol_1 + \frac{(Z - Z_1) * (Vol_1 - Vol_2)}{Z_1 - Z_2}$$

In the second, preferred, embodiment, the volume is given starting from a hyperbolic volume/impedance characteristic, i.e. a relation of the general form Vol=a/(Z+b) or, in other words:

$$Vol = \frac{K_4}{Z - K_5}$$

The two constants $K_4$ and $K_5$ are obtained starting from initial measurements obtained for each patient:

$K_4$ is the constant of proportionality of volume, expressed in milliliters per ohm:

$$K_4 = \frac{(Z_1 - Z_2) * Vol_1}{(1 - (Vol_1 / Vol_2))}$$

$K_5$ represents the level of the asymptote for a volume tending towards infinite, expressed in ohms:

$$K_5 = \frac{(Z_1 - K_4)}{Vol_1}$$

FIG. 2 shows the results of an estimate of the volume carried out in the way indicated above, either by a linear conversion (shown by dashes), or by a hyperbolic conversion (shown by full lines). The squares represent the points of measurement of a test carried out in vitro on a dog heart, documented in the article by Raul Chirife titled "Intracardiac Impedance for Hemodynamic Assessment," Cardiac Pacing, Rome (2004). As one can see, the value of the volume estimated by using a hyperbolic conversion is extremely close to physical reality, though a linear conversion, which is simpler to implement, can also give satisfactory results when less precision is required, or when the range of variation of volume is relatively small that the linear characteristic will suffice.

FIG. 3 illustrates, as for FIG. 2, the results of an estimate of volume carried out in the way indicated above, by a hyperbolic conversion, for two values D=22 mm and D=44 mm of the diameter of a test chamber made of silicone and filled with a saline solution, compared to:
  (i) on the one hand the in vitro values actually measured (squares and stars) and,
  (ii) on the other hand the values resulting from a digital simulation by a finite elements analysis (diamonds and triangles).

The measured and estimated comparative values are documented in the article of K. Hoekstein and G. F. Inbar, titled "Cardiac Systolic Volume Estimate," EE Pub. No 974, February 1994, Technion, Israel. Analysis of this figure shows the relevance of a volume/impedance conversion realized according to the teachings of the invention, particularly of a conversion of a hyperbolic type.

One skilled in the art will appreciate that the present invention can be practiced by other than the described embodiments, which are presented for purposes of illustration and not of limitation.

I claim:

1. An active implantable medical device comprising:
  a plurality of connection terminals able to be connected to electrodes placed in at least three distinct respective sites in a myocardium;
  means for measuring an intracardiac bio-impedance, comprising means for injecting a current, means for collecting a voltage at selected ones of said plurality of connection terminals, and means able to deliver at an output a dynamic impedance signal that is a function of the injected current and the collected voltage; and
  means for evaluating an intracardiac volume, said means receiving at an input the impedance signal and delivering at an output a dynamic value of volume representing an instantaneous absolute value of intracardiac volume, said means further comprising means for converting the impedance signal into a volume according to a hyperbolic characteristic in the form Vol=a/(Z+b), wherein Vol is the value of volume delivered by the means for evaluating, Z is the value of the impedance signal received at input, and a and b are constants.

2. The device of claim 1, further comprising calibration means, for determining constants a and b based upon at least two values of measured volume and at least two values of measured impedance.

3. An active implantable medical device comprising:
  a plurality of connection terminals able to be connected to a plurality of electrodes placed in at least three distinctive sites in a myocardium; and
  means for measuring an intracardiac bio-impedance comprising:
    a current source having an output current pulse;
    a voltage detector having an output signal responsive to a voltage detected at selected ones of said connector terminals in response to an output current pulse;
    a first converter circuit responsive to the detected voltage having an output corresponding to a dynamic impedance signal; and
    a second converter circuit response to the dynamic impedance signal and a conversion algorithm having a dynamic output signal corresponding to an instantaneous absolute value of the intracardiac volume, wherein the conversion algorithm further comprises a hyperbolic characteristic in the form Vol=a/(Z+b) wherein Vol is the instantaneous volume output by the second converter circuit, Z is the dynamic impedance signal output by the first converter circuit, and a and b are constants.

4. The device of claim 3, further comprising calibration means for determining constants a and b based upon at least two values of measured volume and at least two values of measured impedance.

* * * * *